United States Patent [19]

Mader

[11] Patent Number: 5,386,058
[45] Date of Patent: Jan. 31, 1995

[54] METHOD OF PRODUCING POLYMETHINE DYES

[75] Inventor: Roger A. Mader, Stillwater, Minn.

[73] Assignee: Minnesota Mining and Manufacturing Company, St. Paul, Minn.

[21] Appl. No.: 145,789

[22] Filed: Oct. 29, 1993

[51] Int. Cl.$^6$ ............................................. C07C 209/78
[52] U.S. Cl. .......................................... 564/330; 8/659;
544/106; 544/107; 544/178; 546/184; 546/229;
548/577; 564/315; 564/333; 568/58; 568/640;
585/435
[58] Field of Search ............... 585/435; 8/659; 568/58,
568/640; 564/315, 330, 333; 544/106, 107, 178;
546/184, 229; 548/577

[56] References Cited

U.S. PATENT DOCUMENTS

| | | | |
|---|---|---|---|
| 2,813,802 | 11/1957 | Ingle et al. | 428/426 |
| 2,992,938 | 7/1961 | McCarville et al. | 252/587 |
| 3,099,630 | 7/1963 | Wildi et al. | 521/25 |
| 3,275,442 | 9/1966 | Kosenkranius | 430/322 |
| 3,436,353 | 4/1969 | Dreyer et al. | 252/600 |
| 4,547,444 | 10/1985 | Bell et al. | 430/11 |
| 4,939,117 | 7/1990 | Kusakata et al. | 503/224 |
| 4,948,715 | 8/1990 | Hulme-Lowe et al. | 430/495 |
| 5,135,842 | 8/1992 | Kitchin et al. | 430/510 |

FOREIGN PATENT DOCUMENTS 0353007  7/1989  European Pat. Off. .

OTHER PUBLICATIONS

Wizinger et al., Chemische Berichte, 1959, pp. 2309–2320.
Wizinger et al., Helvetica Chimica Acta, vol. 24, Supp. 1941, pp. 369E–388E.
Tuemmler et al., JACS, vol. 80, pp. 3772–3777 (1958).
Lorenz et al., Helvetica Chimica Acta, vol. 28, pp. 600–612 (1945).

*Primary Examiner*—Gary E. Hollinden
*Assistant Examiner*—Scott C. Rand
*Attorney, Agent, or Firm*—Gary L. Griswold; Walter N. Kirn; Gregory A. Everaritt

[57] ABSTRACT

A method for producing polymethine dyes comprising the steps of:
  (a) reacting a 1,1-diaryl-2-metallo-ethene with an ω,ω,-diaryl-polyalkene-aldehyde in an anhydrous solvent under an inert atmosphere; and
  (b) neutralizing the reaction mixture from step (a) with an acid, thereby producing a polymethine dye.

11 Claims, No Drawings

METHOD OF PRODUCING POLYMETHINE DYES

BACKGROUND OF THE INVENTION

1. Field of Invention

This invention relates to a method of preparing certain tetra-aryl-polymethine compounds. These molecules are useful as dyes and sensitizers for thermographic, photographic and photothermographic recording materials.

2. Background of the Art

Polymethine dyes of formula I are well known in the art as having utility in recording materials responsive to a wide range of irradiative energy wavelengths, from thermal exposure to infrared to visible light. U.S. Pat. No. 5,135,842 describes the use of polymethine dyes in thermal dye bleach constructions for imaging and for antihalation layers. U.S. Pat. No. 4,939,117 describes the preparation of pentamethine dyes and their use as leuco dyes. U.S. Pat. No. 4,948,715 and European Patent Application No. 0,353,007 describe the preparation of pentamethine dyes and their use in optical recording.

In polymethine dyes of formula I, typically, $A^1-A^4$ and n are chosen so as to be responsive to particular wavelengths as appropriate for the recording to be done, and include amino groups, alkyl- and aryl-substituted amino groups, alkoxide groups, and other substituents which may advantageously contribute or donate electrons to the polymethine system. Usually, $A^1$ and $A^2$ are identical to each other, and $A^3$ and $A^4$ are identical to each other, and often, due to the method of synthesis of the polymethine system, all four aromatic substituents $A^1-A^4$ are identical. Typically, n is 1, 2, or 3. The counterion $X^-$ can be any of a large number of appropriate anions derived from organic or inorganic acids.

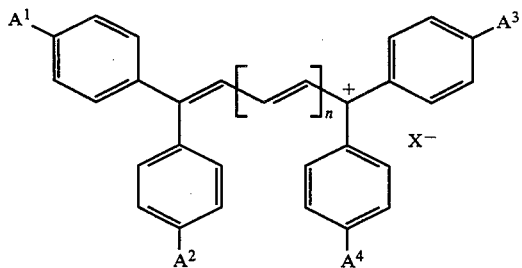

Mixtures of dyes exhibit mixed absorption spectra, which may not be useful in applications requiring absorption at a single, specific wavelength. Purification of mixtures of polymethine dyes obtained from strong acid-catalyzed condensation reactions has proven to be very difficult, relying on selective fractional crystallization methods, which give poor yields, inadequate separations, and often are not reproducible on a production scale. Pure polymethine dyes are needed in the color imaging art for true color reproduction. For example, when used in thermally bleachable antihalation layers of color imaging constructions, impure dyes cause undesirable color to remain after bleaching.

The two well-known methods of synthesis of the pentamethine dye system are described in U.S. Pat. Nos. 4,939,117 and 4,948,715. U.S. Pat. No. 4,939,117 describes a method whereby 2 equivalents of a 1,1-diaryl-ethene are coupled with 1-equivalent of triethylorthoformate in an acid-catalyzed condensation in which water is eliminated and a pentamethine dye salt of formula I is obtained. In this synthesis, substituents $A^1$ and $A^2$ will be, by necessity, identical to $A^3$ and $A^4$ and no possibility exists for formation of a polymethine dye having substituents with $A^1$ and $A^2$ different from $A^3$ and $A^4$. U.S. Pat. No. 4,948,715 describes a method whereby a 1,1-diaryl-ethene is coupled with a 3,3-diaryl-2-propenal in the presence of a strong acid which simultaneously effects condensation and elimination of one water molecule to form a pentamethine dye salt of formula I. In this method, a possibility exists to obtain an tetra-aryl polymethine dye whereby $A^1-A^4$ are different since the substituents on the 1,1-diaryl-ethene could easily be different from those on the 3,3-diaryl-2-propenal. However, mixtures of pentamethine dyes usually result from this method, possibly due to an acid-catalyzed transformylation and equilibration of the aldehyde moiety between the two diaryl-ethenes. The result of this second synthetic method is usually an undesirable mixture of the desired polymethine dye with "crossed-reaction" products having either $A^1$ and $A^2$ groups or $A^3$ and $A^4$ groups on both ends of the polymethine chain.

European Pat. Application 0,353,007 describes the synthesis of pentamethine dyes of formula I in which one of the four A groups is different from the other three identical A groups. These dyes were prepared from the acid-catalyzed condensation of a 1,1-diaryl-ethene in which the two aryl groups in the 1-position were different with a 3,3-diaryl-2-propenal in which both aryl substituents of the aldehyde were identical to one of the aryl substituents of the 1,1-diaryl-ethene.

Thus, although the art provides means of preparing 3,3-diaryl-2-propenal compounds and 1,1-diaryl-ethene compounds, no general means of condensing these compounds in a manner which will ensure the absence of "crossed-reaction" polymethine condensation products has been disclosed. Thus, there is a need for a method of producing tetra-aryl polymethine dyes in good yield which allows preparation of materials without contamination from side reactions that result in the formation of undesired "crossed-reaction" products. Such a method has now been discovered.

SUMMARY OF THE INVENTION

The invention provides a process of preparing α, α, ω, ω-tetra-aryl-polymethine compounds by the reaction of a 1,1-diaryl-2-metallo-ethene with an ω, ω, -diaryl-polyalkene-aldehyde. An advantage of the method of this invention is that α, α, ω, ω-tetra-aryl-polymethine compounds can be prepared which are free from contamination with other α, α, ω, ω-tetra-aryl-polymethine compounds that arise from synthetic procedures known in the art.

The inventive process comprises the steps of:
(a) reacting a 1,1-diaryl-2-metallo-ethene of the formula:

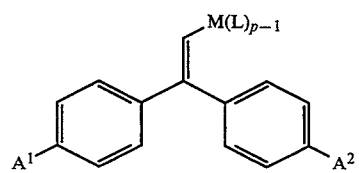

with an ω, ω, -diaryl-polyalkene-aldehyde the formula:

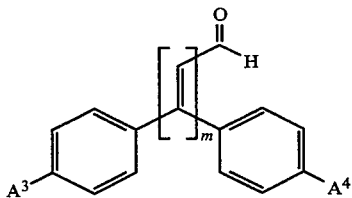

wherein:
- $A^1$, $A^2$, $A^3$, and $A^4$ are independently selected from hydrogen, alkyl groups of up to 10 carbon atoms, cycloalkyl groups of up to 10 carbon atoms, alkoxy and alkylthio groups of up to 10 carbon atoms, $NR^1R^2$, and $NR^3R^4$;
- $R^1$ to $R^4$ are each independently selected from: alkyl groups of up to 20 carbon atoms, alkenyl groups of up to 20 carbon atoms, and aryl groups of up to 14 carbon atoms;
- $R^1$ and $R^2$ together and/or $R^3$ and $R^4$ together may represent the necessary atoms to complete a 5-, 6-, or 7-membered heterocyclic ring group; or one or more of $R^1$ to $R^4$ may represent the atoms necessary to complete a 5- or 6-membered heterocyclic ring group fused to the phenyl ring on which the $NR^1R^2$ or $NR^3R^4$ group is attached;
- M is a metal;
- p is the valence of the metal M;
- m is 1, 2, or 3; and
- L is Cl, Br, or I;

in an anhydrous solvent under an inert atmosphere; and (b) neutralizing the reaction mixture from step (a) with an acid thereby producing a reaction product comprising:

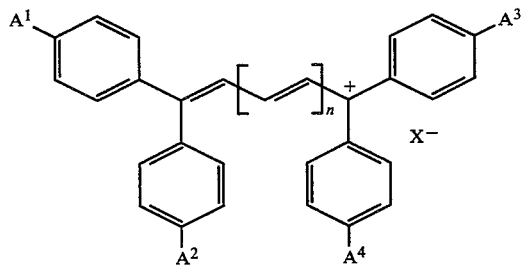

wherein: $A^1$, $A^2$, $A^3$, and $A^4$ are as defined earlier herein; n is 1, 2, or 3; and $X^-$ is the conjugate base of said acid.

In a preferred embodiment, the invention provides a process of preparing 1,1,5,5-tetra-aryl-pentamethine compounds by the reaction of a 1,1-diaryl-vinyl-magnesium halide of the formula:

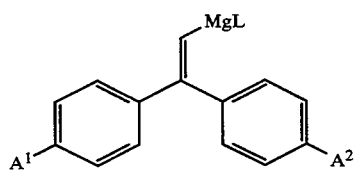

with a 3,3-diaryl-2-propenal of the formula:

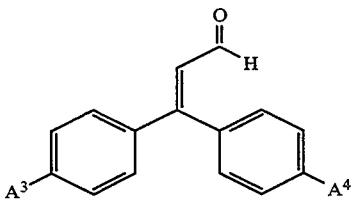

wherein: $A^1$, $A^2$, $A^3$, and $A^4$ are as defined earlier herein.

As is well understood in this area, substitution is not only tolerated, but is often advisable. As a means of simplifying the discussion and recitation of certain terminology used throughout this application, the terms "group" and "moiety" are used to differentiate between chemical species that allow for substitution or which may be substituted and those which do not so allow or may not be so substituted. Thus, when the term "group" is used to describe a chemical substituent, the described chemical material includes the basic group and that group with conventional substitution. Where the term "moiety" is used to describe a chemical compound or substituent, only an unsubstituted chemical material is intended to be included. For example, the phrase "alkyl group" is intended to include not only pure open-chain and cyclic saturated hydrocarbon alkyl substituents, such as methyl, ethyl, propyl, t-butyl, cyclohexyl, adamantyl, octadecyl, and the like, but also alkyl substituents bearing further substituents known in the art. On the other hand, the phrase "alkyl moiety" is limited to the inclusion of only pure open-chain and cyclic saturated hydrocarbon alkyl substituents, such as methyl, ethyl, propyl, t-butyl, cyclohexyl, adamantyl, octadecyl, and the like.

Other aspects, advantages, and benefits of the present invention are apparent from the detailed description, the examples, and the claims.

DETAILED DESCRIPTION OF THE INVENTION

In the compounds of general formula I, $A^1-A^4$ are preferably selected from: $R^1O-$, $R^1S-$, $NR^1R^2$, and $NR^3R^4$; most preferably, alkoxy containing alkyl groups of up to 5 carbon atoms, and dialkylamino bearing alkyl groups of up to 5 carbon atoms.

$R^1$ to $R^4$ are each independently selected from alkyl, and alkenyl groups of up to 20 carbon atoms, preferably of up to 10 carbon atoms, and most preferably of up to 5 carbon atoms and aryl groups of up to 14 carbon atoms, preferably up to 10 carbon atoms. Most often, $R^1=R^2$ and/or $R^3=R^4$ and/or $R^1=R^3$. Preferred examples of $R^1$ to $R^4$ are methyl, ethyl, and 2-methoxyethyl groups. In addition, $R^1$ and $R^2$ together and/or $R^1$ and $R^4$ together may represent the non-metallic atoms necessary to complete a nucleus of a 5-, 6-, or 7-membered heterocyclic ring group. When completing such a ring group the atoms are generally selected from non-metallic atoms such as C, N, O, and S, and each ring group may contain one or more substituents as described above. The heterocyclic ring nuclei so completed may be any of those known in the polymethine dye art, but preferred examples include morpholine, pyrrolidine, 2-methylpiperidine, and azacycloheptane. In addition, one or more of $R^1$ to $R^4$ may represent the necessary atoms to complete a 5- or 6-membered heterocyclic ring fused to the phenyl ring on which the NR$^1$R$^2$ or NR$^3$R$^4$ group is attached. The heterocyclic ring nuclei so completed may be any of those known in the polymethine dye art, but preferred examples include 1,2-dihydroindole, 1,2,3,4-tetrahydroquinoline, and julolidine.

Preferred examples of NR$^1$R$^2$ and NR$^3$R$^2$ are selected from dimethylamino, diethylamino, bis(methoxyethyl)amino, pyrrolidino, morpholino, and azacycloheptyl.

When the groups R$^1$ to R$^4$ are substituted, the substituents may be selected from a wide range of substituents provided that they do not cause autobleaching of the dye or react with the 1,1-diaryl-2-metallo-ethene functionality. For example, substituents having free amino groups promote autobleaching of the polymethine dye unless the amino group is attached directly to the delocalized electron system. Generally the substituents are selected from: cyano groups, ether groups of up to 15 carbon atoms, thioether groups of up to 15 carbon atoms, alkyl groups of up to 15 carbon atoms, alkenyl groups of up to 5 carbon atoms, aryl groups of up to 10 carbon atoms, and heterocyclic ring nuclei comprising up to 10 ring atoms selected from C, N, O, and S, and combinations of these substituents.

In addition to the ring substituents shown in general formula I of the central dye nucleus, the dyes may possess ring substituents in other positions. Non-limiting examples include substituents suitable for the groups R$^1$ to R$^4$; CH$^3$O—; and CH$^3$S—.

In the compounds of formula I, n is 1, 2, or 3; preferably 1 or 2.

In principle, X$^-$ may be any anion that is non-reactive with the polymethine cation. Suitable anions for X$^-$ include inorganic anions such as chloride, bromide, iodide, perchlorate, tetrafluoroborate, triiodide, hexafluorophosphate, and the like. Suitable organic anions include, for example, acetate, 4-toluenesulfonate, and dodecyl-benzenesulfonate, and methanesulfonate. Preferred anions for X$^-$ are those containing a perfluoroalkylsulfonyl group such as, trifluoromethanesulfonate, perfluorooctanesulfonate, and perfluoro(ethylcyclohexane)sulfonate (PECHS).

A feature of the present invention is that a 1,1-diaryl-2-metallo-ethene is caused to react with a ω, ω,-diaryl-polyalkene-aldehyde to produce an isolatable α, α, ω, ω-tetra-aryl-polymethine compound in which substituents on the aryl moieties contributed by the 1-diaryl-2-metallo-ethene may be, and, preferably are, different from substituents on the aryl moieties contributed by the ω, ω,-diaryl-polyalkene-aldehyde. It is an advantage of the present invention that polymethine dyes can be prepared in the absence of competing reactions which might produce impure dyes.

In general the metal M may be any metal whose organometallic compound is known to react with aldehydes. Examples of M are magnesium, lithium, zinc, tin, and copper-lithium (CuLi). Preferred M are magnesium and lithium with magnesium most preferred.

A preferred feature of the present invention is that a 1,1-diaryl-vinylmagnesium halide is caused to react with a 3,3-diaryl-2-propenal to produce an isolatable 1,1,5,5-tetra-aryl-pentamethine compound in which substituents on the aryl moieties contributed by the 1,1-diaryl-vinylmagnesium halide may be, and, preferably are, different from substituents on the aryl moieties contributed by the 3,3-diaryl-2-propenal. Thus, it is a further advantage of the invention that pentamethine dyes can be prepared in the absence of competing reactions which might produce impure dyes.

The 1,1-Diaryl-vinylmagnesium Halide

The preferred 1,1-diaryl-vinylmagnesium halides of formula II comprise one of the starting materials for the method described by the invention. Substituents A$^1$ and A$^2$ may be the same or different, and are as defined earlier herein. As defined earlier herein, L is selected from the group consisting of: Cl, Br, and I.

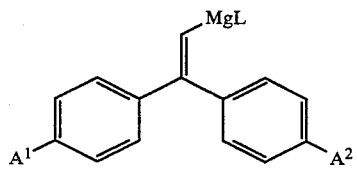

The diaryl vinylmagnesium halide of formula II is obtained by Grignard reaction conditions from the corresponding diaryl-vinyl halide, typically a diaryl-vinyl bromide. The bromide, in turn, is obtained by monobromination of the corresponding 1,1-diaryl-ethene, as described by W. Tadros et al. *J. Chem Soc.*, 1951, 2553. A solution of the 1,1-diaryl-ethene in a solvent such as acetic acid, benzene, carbon tetrachloride, or chlorobenzene is treated with one equivalent of bromine, warmed to effect solution of all reactants, then neutralized and separated from solvent.

The 1,1-diaryl-ethene is obtained by Grignard reaction of methyl magnesium halide with an appropriate benzophenone or diaryl ketone, followed by dehydration, as described in U.S. Pat. No. 4,939,117. The Grignard reagent is prepared from magnesium metal and methyl iodide in dry diethyl ether to which is added the appropriate diaryl ketone under cooled, dry, inert conditions. The resulting alcohol is treated with a drying agent in an appropriate solvent, such as benzene, to effect dehydration, and the desired 1,1-diaryl-ethene is isolated by evaporation of the solvent.

A wide variety of substituted benzophenones is available commercially. In addition, benzophenones not readily available commercially can be produced by well-documented methods which are not the subject of the present invention. The reaction scheme for the preparation of the 1,1-diaryl-vinylmagnesium halide is shown in Scheme 1.

Scheme 1

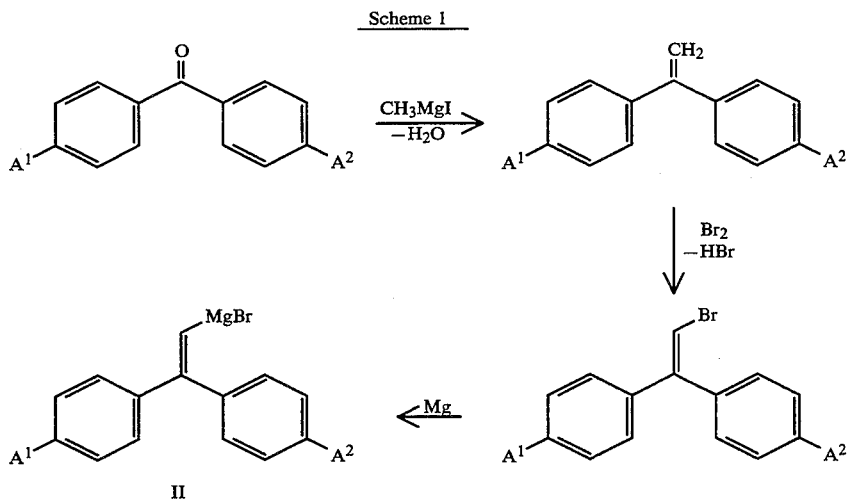

The 3,3-Diaryl-2-propenal

The preferred 3,3-diaryl-2-propenals useful in the invention are α, β-unsaturated aldehydes bearing two aryl groups on the carbon atom farthest from the aldehyde moiety. The aldehydes are readily obtained by formylation of a 1,1-diaryl-ethene by common laboratory procedures, e.g., the well known Vilsmeier formylation which uses phosphorous oxychloride in dimethylformamide. The 3,3-diaryl-2-propenal compounds are represented by formula III, wherein $A^3$ and $A^4$ are as defined earlier herein.

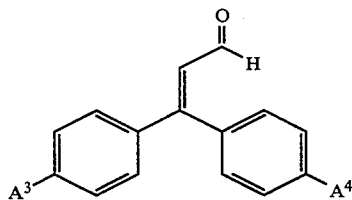

The Grignard alkylation of a diaryl aldehyde of formula III with a vinyl-magnesium halide of formula II has not heretofore been described. It provides an excellent method of forming tetra-aryl-polymethine dyes in good yield and without the possibility for unwanted side reactions, advantages not available until the present invention. The Grignard reaction is carried out in dry solvent under an inert atmosphere, and proceeds smoothly to give, after neutralizing the reaction mixture, a tetra-aryl-pentamethine alcohol or salt thereof. The reaction is shown in Scheme 2.

Scheme 2

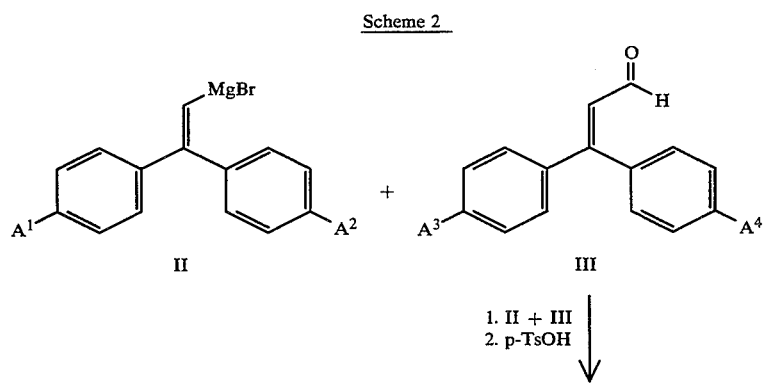

Scheme 2
-continued

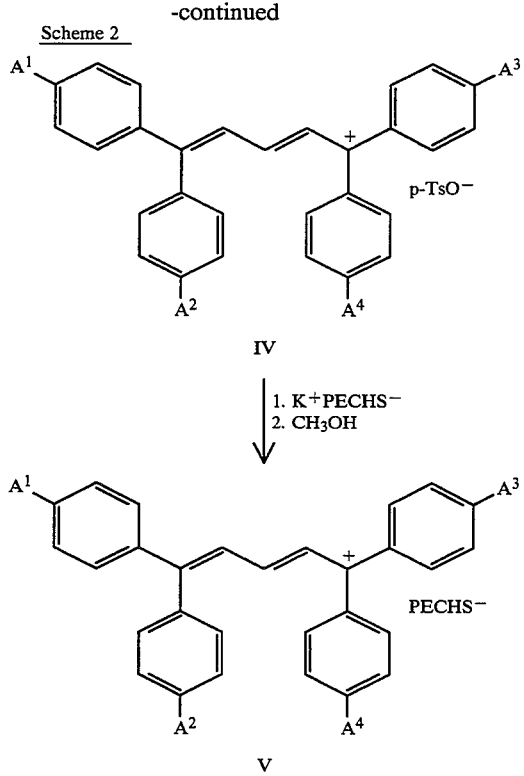

KPECHS = Potassium perfluoro(4-ethylcyclohexyl)sulfonate

The mild conditions and rapid rate of the Grignard reaction, as shown in Scheme 2, preclude equilibration of the reactants, so "crossed-reaction" products will not be obtained. The p-toluenesulfonate salt obtained (IV) is drawn as one of canonical form of the many resonance hybrids possible. The major contributor will, of course, depend on the relative electron-donating capacity of the aryl substituents $A^1$–$A^4$. Similarly, the PECHS salt (V) is a resonance hybrid of which V is merely one canonical form.

That the perfluoro(4-ethylcyclohexyl)sulfonate (PECHS salt) V, $A^1=A^2=OCH_3$; $A^3=N(CH_3)_2$; $A^4=H$, as described below, is indeed on compound, free from "crossed-reaction" products, is shown by its NMR spectrum. A total of exactly 6 —$OCH_3$ hydrogens ($\delta=3.87$ and $3.84$) and 6 —$N(CH_3)_2$ hydrogens ($\delta=3.42$) are seen, in the ratio of 1:1:2, respectively. In contrast, the NMR spectrum of the condensation product of the Comparative Example, prepared by acid-catalyzed condensation of a 1,1-diaryl-ethene with a 3,3-diaryl-2-propenal, exhibited a strong absorption attributed to additional —$N(CH_3)_2$ protons. Often, this signal was seen to be equal in intensity to that of the signal at $\delta=3.42$, indicating the significant presence of "crossed-reaction" product impurities.

Objects and advantages of this invention will now be illustrated by the following examples, but the particular materials and amounts thereof recited in these examples, as well as other conditions and details, should not be construed to unduly limit this invention. All percentages are by weight unless otherwise indicated.

EXAMPLES

Preparation of 1-(p-N,N-Dimethylamino)phenyl-1-phenyl-ethene

A solution of 240.06 g 4-dimethylaminobenzophenone (Aldrich) in 1000 ml tetrahydrofuran (THF) was added slowly at room temperature to 1600 ml of 1.4 molar methylmagnesium bromide in THF, under a nitrogen stream, over a five-hour period. The reaction temperature was kept below 32° C. during the addition. After stirring overnight under nitrogen, the reaction was quenched by very careful addition of 400 ml water, dropwise, with ice-bath cooling to keep the temperature under 25° C. When all of the water had been added, 600 ml ethyl acetate were added to the flask, and stirring was continued for 30 minutes. The liquid materials were separated from the solid residues by vacuum transfer of the liquids into an Erlenmeyer flask via a sintered glass dip tube, and the remaining solids were washed with 200 ml ethyl acetate. The solution was then stripped of solvent via rotary evaporation and the residue was taken up in 1000 ml toluene, mixed with 530 ml water and 530 ml acetic acid, then heated at 50° C. for 3 hours to effect dehydration. On cooling, the organic phase was separated, washed with 2×430 ml water, then dried over approx. 60 g magnesium sulfate. Filtration and removal of solvent gave 278 g 1-(p-N,N-dimethylamino)phenyl-1-phenyl-ethene which crystallized on cooling. NMR of the crystalline material confirmed the desired structure.

Preparation of 1,1-di(p-methoxyphenyl)-ethene

A solution of 258 g 4,4'-dimethoxybenzophenone in 3000 ml warm toluene was added to 1600 ml 1.4M methylmagnesium bromide under nitrogen with stirring, over a one-hour period. The reaction temperature was kept below 40° C. After addition was complete, stirring was continued for one hour at 30°–40° C. and two hours at 50° C. The mixture was cooled to room temperature and poured into a stirred mixture of 400 ml acetic acid and 624 g ammonium chloride in 7200 ml deionized water. After gas evolution and exotherm had subsided, the organic (toluene) phase was separated and the aqueous phase was washed with 2×600 ml toluene. The combined toluene phases were washed with 1×2400 ml water, then placed in a flask and treated with a solution of 1470 ml deionized water and 1470 ml acetic acid at 50° C. for three hours to effect dehydration of the intermediate hydroxy compound. On cooling, the phases were separated and the toluene phase was washed with 2×1000 ml deionized water, then dried over magnesium sulfate. Filtration and removal of toluene gave a slightly wet cake which was triturated with 1400 ml diethyl ether, filtered and dried to give 222 g 1,1-di(p-methoxyphenyl)-ethene, m.p. 141°–143° C. whose structure was also confirmed by NMR.

Preparation of 1,1-Di(p-methoxyphenyl)-2-bromo-ethene

To a stirred solution of 24.0 g 1,1-di(p-methoxyphenyl)-ethene (prepared above) in 200 ml benzene was added 24.0 g bromine over a 45 minute period. On heating the reaction mixture to reflux, HBr gas was evolved. Heating was continued until gas evolution ceased. Removal of solvent and recrystallization from hexane gave 27.5 g 1,1-di(p-methoxyphenyl)-1-bromo-ethene, whose structure was confirmed by NMR.

Preparation of 3-(p-N,N-Dimethylamino)phenyl-3-phenyl-propenal Compound III; $A^3$=N(CH$_3$)$_2$, $A^4$=H A solution of 136 g 1-p-dimethylaminophenyl-1-phenyl-ethene (prepared above) in 484 ml methylene chloride was added over a 30 minute period to an ice-cooled solution of 340 ml dimethylformamide in 972 ml methylene chloride to which had been added, slowly, with cooling, 93.8 g phosphorous oxychloride. The reaction mixture was allowed to warm to room temperature, with stirring, then stirred an additional 30 minutes. A total of 1214 ml saturated aqueous sodium acetate solution was slowly added to the stirred reaction mixture with cooling, followed by slow addition of 486 ml of 50% aqueous, NaOH. Addition of the NaOH solution was done at such a rate so as to maintain reflux. After addition was complete, the reaction was stirred for 30 minutes, then cooled to room temperature and admixed with 4000 ml water and 2915 ml methylene chloride. The organic phase (bottom) was separated, and the aqueous phase was washed with 3×400 ml methylene chloride. The combined organic phases were washed with 3×800 ml water, dried over magnesium chloride, filtered and evaporated to give 61 g of a yellow solid, m.p. 140°–141° C. Structure was confirmed by NMR.

Preparation of 1,1-di(p-methoxyphenyl)-5-(p-N,N-dimethylamino)-phenyl5-phenyl-pentamethine p-toluene sulfonate Compound IV; $A^1$=$A^2$=O(CH$_3$); $A^3$=N(CH$_3$)$_2$; $A^4$=H A solution of 8.0 g of 1,1-di(p-methoxyphenyl)-2-bromo-ethene, prepared above, in 70 ml dry THF was slowly added to a stirred suspension of 0.60 g magnesium turnings in 10 ml dry THF over a 75 minute period during which the reaction temperature was maintained at 50° C. When addition was complete, the reaction mixture was cooled to 25° C. then treated with a solution of 5 g of 3-(p-N,N-dimethylamino)phenyl-3-phenyl-2-propenal in 40 ml dry THF over a 30 minute period, while the reaction temperature was maintained at 25° C. The liquid portion of the reaction mixture was decanted from residual magnesium turnings and treated with 9.5 g of p-toluenesulfonic acid (p-TsOH). A precipitate formed and the reaction mixture was treated with 100 ml THF and filtered. The collected solid reaction product was slurried in 200 ml THF then collected by filtration and dried to give 11.3 g of crude compound IV, $A^1$=$A^2$=OCH$_3$; $A^3$=N(CH$_3$)$_2$; $A^4$=H. The compound was used without further purification.

Preparation of 1,1-di(p-methoxyphenyl)-5,5-di(p-N,N-dimethylamino phenyl)-pentamethine p-toluenesulfonate Compound IV: $A^1$=$A^2$=OCH$_3$; $A^3$=$A^4$=N(CH$_3$)$_2$ In the manner described above, 1,1-di(p-methoxyphenyl)-2-bromo-ethene was converted to the corresponding Grignard reagent and reacted with 3,3-di(p-N,N-dimethyl-aminophenyl)-2-propenal. The structure of the resulting polymlethine dye salt was confirmed by NMR.

Preparation of 1,1-di(p-methoxyphenyl)-5-(p-N,N-dimethylamino)-phenyl-5-phenyl-pentamethine perfluoro(4-ethylcyclohexyl)sulfonate Compound V: $A^1$=$A^2$=OCH$_3$; $A^3$=N(CH$_3$)$_2$; $A^4$=H A total of 2.4 g potassium perfluoro(4-ethylcyclohexyl)sulfonate (KPECHS, available from 3M Co., St. Paul, MN) was stirred thoroughly in methyl alcohol, and the slurry was filtered to remove impurities. The resulting KPECHS solution was added to a solution of 2.8 g of p-toluenesulfonate salt IV ($A^1$=$A^2$=OCH$_3$; $A^3$=N(CH$_3$)$_2$; $A^4$=H) in 60 ml of methyl alcohol, and the mixture was heated to 50° C. for ten minutes, then cooled to room temperature and finally diluted with 40 ml water. An oil formed, which solidified on standing. The amorphous solid was separated from the aqueous methyl alcohol and taken up in methylene chloride, which allowed the separation of residual water. Evaporation of methylene chloride gave 1.2 g of 1,1-di(p-methoxyphenyl)-5-(p-N,N-dimethylamino)phenyl-5-phenylpentamethine perfluoro(4-ethylcyclohexyl)sulfonate (V) as a crystalline solid. The structure was confirmed by NMR.

Comparative Example

The following example demonstrates the synthesis of a pentamethine dye via the reaction of 1,1-bis(p-methoxyphenyl)-ethene with 3-(p-N,N-dimethlamino)-phenyl-3-phenyl-2-propenal in the presence of a strong acid.

A solution of 43.85 g of 3-(p-N,N-dimethylaminophenyl)-3-phenyl-2-propenal and 35.77 g of 1,1-bis(p-methoxyphenyl)-ethene in a mixture of 623 ml acetic anhydride and 312 ml glacial acetic acid was stirred for 15 minutes, then treated with 31.2 g of p-toluenesulfonic acid and an additional 146 ml acetic anhydride. The mixture was stirred and heated to 45° C. for 16 hours, then cooled to room temperature and treated with 1923 ml diethyl ether. A solid product formed which was separated by decanting. Trituration of the semi-solid with additional diethyl ether produced a fine particulate solid product which was collected by filtration, washed with additional diethyl ether and dried to give 75 g of a solid blue dye.

This solid was taken up in 970 ml methyl alcohol and treated with a prepared solution of 60 g potassium perfluoro(4-ethylcyclohexyl)sulfonate which had been taken up in 583 ml methyl alcohol at 40° C. and filtered to remove insoluble impurities. After standing for about 60 minutes, the methanol solution was poured into 1455 ml deionized water and the resulting blue solid was collected and washed with a 40% water/methyl alcohol solution. On drying at 80° C. in a vacuum oven over night, 78 g of a blue solid was obtained. The NMR spectrum of the solid showed absorptions of equal intensity at δ=3.14 ("crossed-reaction" adduct) and δ=3.25 (desired reaction adduct) indicative of a dye mixture.

The present invention has been described with reference to various specific and preferred embodiments and techniques. It should be understood, however, that many variations and modifications may be made while remaining within the spirit and scope of the present invention as defined in the claims.

What is claimed is:

1. A process comprising the steps of:
   (a) reacting a 1, 1-diaryl-2-metallo-ethene of the formula:

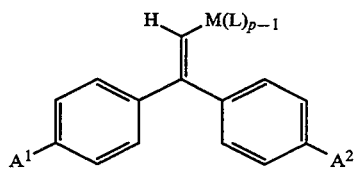

with an ω, ω-diaryl-polyalkene-aldehyde of the formula:

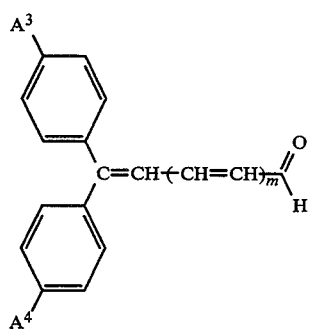

wherein:
   $A^1$, $A^2$, $A^3$, and $A^4$ are independently selected from: hydrogen, alkyl groups of up to 10 carbon atoms, cycloalkyl groups of up to 10 carbon atoms, alkoxy and alkylthio groups of up to 10 carbon atoms, $NR^1R^2$, and $NR^3R^4$;
   $R^1$ to $R^\alpha$ are each independently selected from: alkyl groups of up to 20 carbon atoms, alkenyl groups of up to 20 carbon atoms, and aryl groups of up to 14 carbon atoms;
   $R^1$ and $R^2$ together and/or $R^3$ and $R^4$ together may represent the necessary atoms to complete a 5-, 6-, or 7-membered heterocyclic ring group; or one or more of $R^1$ to $R^4$ may represent the atoms necessary to complete a 5- or 6-membered heterocyclic ring group fused to the phenyl ring on which the $NR^1R^2$ or $NR^3R^4$ group is attached with the proviso that $NR^1R^2$ or $NR^3R^4$ do not react with the 1,1-diaryl-2-metallo-ethene;
   M is magnesium, lithium, zinc, tin, or copper-lithium;
   p is the valence of the metal M;
   m is 0, 1, or 2; and
   L is Cl, Br, or I;
   in an anhydrous solvent under an inert atmosphere; and
   (b) neutralizing the reaction mixture from step (a) with an acid thereby producing a reaction product comprising:

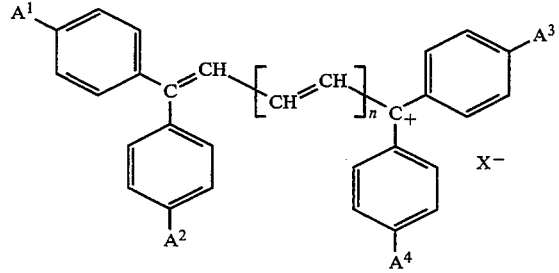

wherein: n is 1, 2, or 3; and $X^-$ is the conjugate base of said acid.

2. The process of claim 1 wherein the 1,1-diaryl-2-metallo-ethene is a vinylmagnesium halide of the formula:

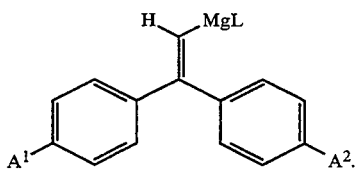

3. The process of claim 1 wherein the ω, ω-diaryl-polyalkene-aldehyde is a 3,3-diaryl-2-propenal of the formula:

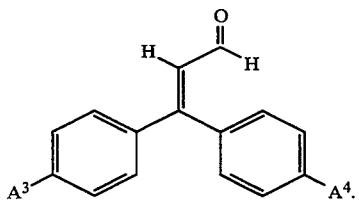

4. The process of claim 1 further comprising the step of reacting said product of step (b) with potassium perfluoro (4-ethylcyclohexyl)sulfonate.

5. The process according to claim 1 wherein:
   $R^1$ to $R^4$ are each independently selected from: alkyl groups of up to 10 carbon atoms and alkenyl groups of up to 10 carbon atoms; or
   $R^1$ and $R^2$ together and/or $R^3$ and $R^4$ together may represent the necessary non-metallic atoms to complete a heterocyclic ring group comprising up to 6 atoms selected from C, N, O, and S.

6. The process according to claim 1 wherein:
   $A^1$, $A^2$, $A^3$, and $A^4$ individually represent alkoxy groups of up to 5 carbon atoms, $NR^1R^2$, and $NR^3R^4$; and
   $R^1$ to $R^4$ are each independently selected from the group consisting of: methyl, ethyl, and methoxyethyl groups; or $R^1$ and $R^2$ together and/or $R^3$ and $R^4$ together represent the necessary non-metallic ring atoms to complete a morpholine, piperidine, or pyrrolidine ring; or, any of $R^1$ to $R^\alpha$ may represent the necessary atoms to complete a 5- or 6-membered heterocyclic ring fused to the phenyl ring on which the $NR^1R^2$ or $NR^3R^4$ group is attached.

7. The process according to claim 1 where L is Br.

8. The process according to claim 1 wherein said acid in (b) has a pKa of less than about 1.0.

9. The process according to claim 1 wherein said acid in (b) is selected from the group consisting of: sulfuric, toluenesulfonic, methanesulfonic, perchloric, trifluoromethanesulfonic, trifluoroacetic, hydrochloric, and hydrobromic acids.

10. The process according to claim 1 wherein step (a) is conducted at a temperature of from about -25° C. to room temperature.

11. The process according to claim 1 wherein M is magnesium.

* * * * *